(12) United States Patent
Cheng et al.

(10) Patent No.: US 10,799,474 B2
(45) Date of Patent: Oct. 13, 2020

(54) METHOD OF TREATING LEUKEMIA UTILIZING SOMATIC CELL REPROGRAMMING

(71) Applicant: Institute of Hematology and Blood Diseases Hospital, CAMS & PUMC, Tianjin (CN)

(72) Inventors: Tao Cheng, Tianjin (CN); Hui Cheng, Tianjin (CN); Yajie Wang, Tianjin (CN); Hongyan Zhang, Tianjin (CN); Yawei Zheng, Tianjin (CN); Sha Hao, Tianjin (CN)

(73) Assignee: Institute of Hematology and Blood Disease Hospital, CAMS & PUMC, Tianjin (CN)

( * ) Notice: Subject to any disclaimer, the term of this patent is extended or adjusted under 35 U.S.C. 154(b) by 214 days.

(21) Appl. No.: 15/751,166

(22) PCT Filed: Jul. 22, 2016

(86) PCT No.: PCT/CN2016/091023
§ 371 (c)(1),
(2) Date: Feb. 8, 2018

(87) PCT Pub. No.: WO2017/185542
PCT Pub. Date: Nov. 2, 2017

(65) Prior Publication Data
US 2018/0228763 A1    Aug. 16, 2018

(30) Foreign Application Priority Data

Apr. 28, 2016   (CN) .......................... 2016 1 0280410

(51) Int. Cl.

| | | |
|---|---|---|
| *A61K 31/352* | (2006.01) | |
| *A61K 31/506* | (2006.01) | |
| *A61K 31/19* | (2006.01) | |
| *A61K 38/17* | (2006.01) | |
| *A61K 31/135* | (2006.01) | |
| *A61K 31/7105* | (2006.01) | |
| *A61K 31/711* | (2006.01) | |
| *A61K 31/444* | (2006.01) | |
| *A61K 31/137* | (2006.01) | |
| *A61P 35/02* | (2006.01) | |
| *A61K 31/192* | (2006.01) | |
| *A61K 31/4375* | (2006.01) | |
| *A61K 31/519* | (2006.01) | |
| *A61K 45/06* | (2006.01) | |

(52) U.S. Cl.
CPC .......... *A61K 31/352* (2013.01); *A61K 31/135* (2013.01); *A61K 31/137* (2013.01); *A61K 31/19* (2013.01); *A61K 31/192* (2013.01); *A61K 31/4375* (2013.01); *A61K 31/444* (2013.01); *A61K 31/506* (2013.01); *A61K 31/519* (2013.01); *A61K 31/711* (2013.01); *A61K 31/7105* (2013.01); *A61K 38/1709* (2013.01); *A61K 38/1761* (2013.01); *A61K 45/06* (2013.01); *A61P 35/02* (2018.01)

(58) Field of Classification Search
CPC .. A61K 31/352; A61K 31/135; A61K 31/137; A61K 31/19; A61K 31/192; A61K 31/4375; A61K 31/444; A61K 31/506; A61K 31/519; A61K 31/7105; A61K 31/711; A61K 38/1709; A61K 38/1761; A61K 45/06; A61P 35/02
See application file for complete search history.

(56) References Cited

FOREIGN PATENT DOCUMENTS

| | | |
|---|---|---|
| CN | 105833275 | 8/2016 |
| WO | 2016033160 | 3/2016 |

OTHER PUBLICATIONS

Ito et al., Cancer Res. 64: 1071-1078, 2004.*
Kang et al., Cell Stem Cell 5: 135-138, Aug. 7, 2009, including Supplemental Data (pp. 1-14).*
Choi et al., Scientific Reports, 5: 1-8, 2015.*
Kay, Nature Reviews Genetics, advance online publication, pp. 1-13, published online Apr. 6, 2011.*
Misra, JAPI, 61: 127-133, 2013.*
Liu et al., Leukemia (2014) 28, 1071-1080.*
Carette et al., Blood. 2010;115(20): 4039-4042.*
Quan et al., "Establishing of the Optimization of Mouse (*Mus musculus*) STO Cell Lines Reprogram to Pluripotent Stem Cells," Journal of Agricultural Biotechnology, Oct. 2012, pp. 1159-1167.
"International Search Report (Form PCT/ISA/210)", dated Jan. 22, 2017, with English translation thereof, pp. 1-6.

* cited by examiner

*Primary Examiner* — Thaian N. Ton
(74) *Attorney, Agent, or Firm* — JCIPRNET

(57) ABSTRACT

The present invention provides a method for treating leukemia utilizing somatic cell reprogramming. The method includes a step of introduction of somatic cell reprogramming inducing factors Oct-4, Sox-2, Klf4 and c-Myc (OSKM for short) into leukemic cells or a step of utilizing small reprogramming molecules in in-vitro culture. It promotes leukemic cells to initiate process of somatic cell reprogramming in order to induce apoptosis and finally purpose of eliminating leukemic cells in-vivo or in-vitro is achieved. It provides new ideas and methods for clinical treatment of leukemia in the future.

6 Claims, 7 Drawing Sheets

CD34+ cells from umbilical cord blood

CD34+ cells from AML patients

METHOD OF TREATING LEUKEMIA UTILIZING SOMATIC CELL REPROGRAMMING

CROSS-REFERENCE TO RELATED APPLICATION

This application is a 371 of international application of PCT application serial no. PCT/CN2016/091023, filed on Jul. 22, 2016, which claims the priority benefit of China application no. 201610280410.5, filed on Apr. 28, 2016. The entirety of each of the above-mentioned patent applications is hereby incorporated by reference herein and made a part of this specification.

BACKGROUND OF THE INVENTION

1. Technical Field

The present invention relates to a method of treating the leukemia by utilizing cell reprogramming.

2. Description of Related Art

Somatic cell reprogramming refers to a process of utilizing a specific method to revert the differentiated somatic cells back to pluripotent or totipotent states. In 2006, a Japanese scientist Shinya Yamanaka verified that over-expression of four transcription factors OSKM (Oct4, Sox2, Klf4 and c-Myc) enables the differentiated cells to regain pluripotency, this type of cells has biological characteristics that are very similar to the embryonic stem cell, he named it as induced pluripotent stem cell (iPSCs), and was awarded the Nobel Prize in Physiology or Medicine in 2012 for the findings. Since the establishment of iPSCs technology, it has a very broad prospect of applications in the fields of fundamental research, pathogeneses, drug screening and clinical treatment, etc.

During early iPSCs technology, techniques of retrovirus or lentivirus are mainly utilized to promote the expression of the exogenous reprogramming factor of OSKM. In consideration that direct virus infection can increase the mutation of somatic cells, and the virus vector which are able to integrate into the genome directly in the iPSCs will be expressed as the cells differentiate, and ultimately affects the applications and researches of iPSCs. Regarding the method of inducing the reprogramming factors, scientists have developed a variety of non-integrated methods. At the level of DNA, scientists utilized the technologies of episomal plasmid, Sendai virus, transposon, etc. to realize the induced expression of OSKM, however, the reprogramming efficiency of these methods are different, and several passages are needed to obtain iPSCs without carrying vectors. At the level of RNA, Warren et al. introduced an in-vitro transcribed mRNA of OSKM directly into the fibroblasts to obtain iPSCs, this method has certain level of technical difficulty and requires several transfections, although it is able to effectively produce iPSCs without carrying vectors. At the level of protein, Kim et al. used a cell penetrating peptide to introduce OSKM into the cell and successfully obtained the iPSCs from human renal fibroblasts, this method involves no genetic material at all but its inducing efficiency is low. In addition, compounds of small reprogramming molecules can be added into the reprogramming system to inhibit or activate some signal pathways in order to significantly improve the reprogramming efficiency, or even the classical reprogramming factors can be replaced by a variety of small reprogramming molecules to realize the reprogramming. The abovementioned methods without genome integration greatly drive the prospect of clinical applications of iPSCs.

Although normal cells can be effectively reprogrammed in-vivo to become iPSCs, currently there is no study reporting whether tumor cells can be reprogrammed to become iPSCs in vivo. Similar to malignant tumor, generation of iPSCs is inhibited by the pathways of tumor suppressor genes such as p53 and Rb. Both c-Myc and Klf4 among the reprogramming factors are famous oncogenes. Moreover, studies have demonstrated that the transient expression of reprogramming factors in vivo led to cancer development in various tissues. Thus, there is similarity between tumorigenesis and reprogramming of somatic cells. Compared to normal somatic cells, the tumor cell reprogramming is more difficult with extremely low efficiency, but the mechanism remains ambiguous.

Leukemia is a malignant tumor of blood system. According to the statistics, morbidity of leukemia ranked number 6 among various tumors and ranked number 1 in pediatric tumors in China. According to the onset of urgency and the cell type, leukemia can be divided into many types. So far, leukemic cells are mainly eliminated from the body through targeted drug chemotherapy or immunotherapy. However, a broad-spectrum therapy for treating several types of leukemias is not available. There are few cases of successful reprogramming of leukemic cells into iPSCs, suggesting that leukemic cells are difficult to undergo effective reprogramming, although the mechanism thereof is not reported. During the process of reprogramming, since genetics and epigenetic modification change drastically, some cells will undergo apoptosis. It is found in the present invention that during the process of leukemic cells reprogramming, majority of the cells undergo apoptosis, it directly related to the difficulty of leukemic cells to become iPSCs. By utilizing such characteristics of leukemic cells and combining the reprogramming technology, it may provide new ideas and methods for treating leukemia.

BRIEF SUMMARY OF THE INVENTION

The technical issue to be solved by the present invention is to selectively eliminate leukemic cells in-vivo or in-vitro by utilizing cell reprogramming.

The present invention employs technical solutions as follows:

The present invention provides a type of inducing factors (i.e., reprogramming factors) Oct-4, Sox-2, Klf4 and c-Myc (OSKM for short) to be used to promote apoptosis of leukemic cells in-vivo or in-vitro.

In this application, the inducing factors Oct-4, Sox-2, Klf4 and c-Myc promote the leukemic cells to initiate reprogramming process.

The leukemic cells are leukemic cells of mammals (including human), preferably human leukemic cells.

The inducing factors are in the form of cDNA, mRNA or protein.

The present invention further provides a method of inducing apoptosis of leukemic cells in-vivo or in-vitro by utilizing cell reprogramming, the method includes a step of introducing reprogramming factors Oct-4, Sox-2, Klf4 and c-Myc (OSKM for short) into leukemic cells. Thus, reprogramming process of the leukemic cells is initiated.

The present invention further provides a method of treating leukemia by utilizing cell reprogramming, the method includes a step of introducing reprogramming factors Oct-4, Sox-2, Klf4 and c-Myc (OSKM for short) into leukemic cells. Through high expression of OSKM genes in the leukemic cells, reprogramming process of the leukemic cells is initiated, and thus apoptosis of the leukemic cells is induced, purpose of eliminating the leukemic cells in-vivo or in-vitro can be achieved.

Preferably, the introducing method employs methods of virus infection, recombinant protein transfection or vector transfection by electroporation.

The methods of virus infection, recombinant protein transfection or vector electroporation mentioned in the present invention are conducted according to conventional methods in the art.

For example, the step of virus infection includes transfection of virus vector containing Oct-4, Sox-2, Klf4 and c-Myc and its corresponding packaging vector to the packaging cell line (such as 293T, 293A, etc.), after virus production, harvest the corresponding viruses and add the corresponding virus into culture medium of leukemic cells for infection, wherein the virus vector is selected from lentivirus vector, retrovirus vector, adenovirus vector or Sendai virus vector.

For example, the step of recombinant protein transfection includes: recombinant proteins of Oct-4, Sox-2, Klf4 and c-Myc with penetrating peptide are mixed, and are added into the leukemic cell culture system for reprogramming induction.

For example, the step of vector electroporation includes: using method of electroporation, transfect episomal plasmid carrying reprogramming factors into the leukemic cells by the method of e electroporation, so that the leukemic cells are with high transient expression of the reprogramming factors (OSKM). Specifically, steps are as follows: conduct nucleus transfection using Amaxa Nucleofector apparatus (conduct according to operating manual), with process (whole duration shall not exceed 15 mins) of: add 100 μl of prepared electro-transfection buffer into a 15 ml centrifuge tube containing $5\times10^5$ leukemic cells, subsequently, and add a prepared plasmid, including 10 μg pEV SFFV/EF1/CAG-OS and 5 μg pEV SFFV/EF1/CAG-MK, after mixing evenly transfer into a transfection cuvette, place into a transfection chamber to conduct electroporation.

The present invention further provides a method of inducing apoptosis of leukemic cells in-vivo or in-vitro by utilizing cell reprogramming, the method includes a step of utilizing small reprogramming molecules in in-vitro culture. It promotes initiation of reprogramming process of the leukemic cells.

The present invention further provides a method of treating leukemia by utilizing the cell reprogramming, the method includes a step of utilizing small reprogramming molecules in in-vitro culture. It promotes initiation of reprogramming process of the leukemia cells and thus induces apoptosis of the leukemic cells, purpose of eliminating the leukemic cells in-vitro can be achieved.

The small reprogramming molecules are one or a combination of two or more of forskolin (FSK, F), VPA (V), CHIR99021 (CHIR, C), RepSox (616452, 6), tranylcypromine (TCP, T) and TTNPB (N).

Preferably, the small reprogramming molecules are a combination of six of forskolin (FSK, F), VPA (V), CHIR99021 (CHIR, C), RepSox (616452, 6), tranylcypromine (TCP, T) and TTNPB (N).

The leukemic cells according to the present invention are leukemic cells from the host of mammals (including human), preferably human leukemic cells.

The beneficial effects of the present invention are:
The present invention utilizes cell reprogramming, enable the elimination of leukemic cells in-vivo or in-vitro effectively and selectively, and thus providing new ideas and methods for clinical treatment of leukemia in the future.

DETAILED DESCRIPTION OF THE INVENTION

In order to understand the present invention, the following embodiments are integrated to further describe the present invention, but are not intended to limit the protection scope of the present invention.

Embodiment 1

Utilizing Reprogramming Factor to Eliminate Mouse Leukemic Cells In-Vivo/In-Vitro 1. Preparation of leukemia retrovirus: method with lipofectamine2000 was used in preparation of retrovirus. 293T cells were cultured in 10 cm culture dish, when the cells reached a confluency of 90%, plasmids and lipofectamine2000 mixture were added. The plasmids include: packaging plasmids (pKat and pVSVG) and target plasmid of retrovirus (MSCV-MLL/AF9-IRES-GFP). Viral supernatants were collected at 48-hour and 72-hour respectively. Amicon Ultra-15 centrifugal filter devices (100K NMWL) was used for concentration.

2. Preparation of mouse acute myeloid leukemic cells: bone marrow cells were obtained from OSKM mice (or known as 'all-iPS' mice, the mice were developed by Professor Shaorong Gao's Laboratory, article source: Kang, L. et al. Cell Stem Cell. 2009;5:135-138.) and lineage-negative (Lin−) bone marrow cells were enriched by method using magnetic beads. Retrovirus carrying MLL-AF9 fusion gene was added into Lin− cell culture medium, after infecting for 48 hours, the infected cells were collected, and transplanted into the tail vein of lethally irradiated C57BL/6J mice. After onset of leukemia, leukemic cells from the spleens and bone marrows of the mice were collected. Since the leukemic cells were obtained from the OSKM mice, thus the expression of OSKM in the leukemic cells could be activated by doxycycline (Dox).

Figure 1A:
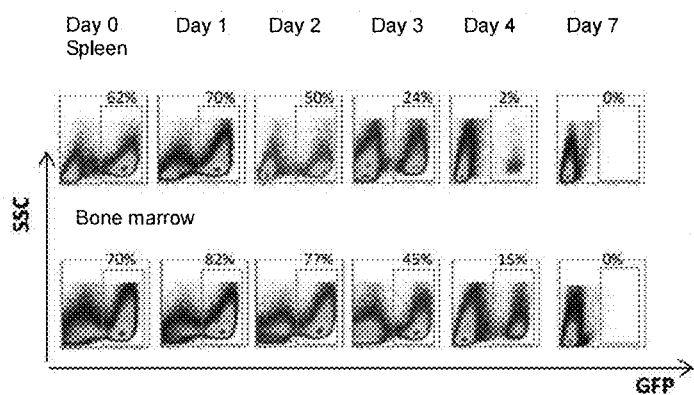
FIGS. 1A, 1B, and 1C—Analysis on ratio of leukemic cells in mouse spleen and bone marrow after adding Dox into the drinking water for leukemic mice.
Figure 1B:
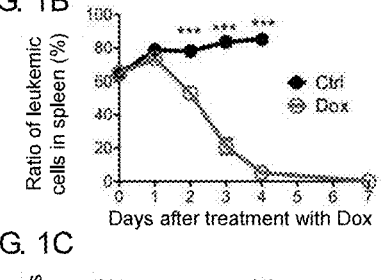
Figure 1C:
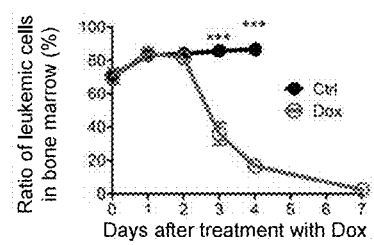

3. Elimination of leukemic cells in-vivo: leukemic cells were transplanted into the tail vein of lethally irradiated C57BL/6J mice. In the late stage of leukemia (leukemic cells exceeded 70% in bone marrow), the mice were divided into two groups, nothing was added into the drinking water of mice in control group, Dox (concentration of 1 mg/ml) was added into the drinking water of mice in experimental group, and for 7 consecutive days. The results are as shown in FIGS. 1A, 1B, and 1C, in FIG. 1A, the result of flow cytometry showed that the number of leukemic cells in the spleen and bone marrow of the mice in the experimental group decreased gradually. FIGS. 1B and 1C showed the ratios of leukemic cells in the bone marrow and spleen, respectively. It is shown that the ratios of leukemic cells in the spleen and bone marrow of the control group increased gradually, the ratios of leukemic cells in the spleen and bone marrow of the experimental group decreased gradually until unable to be determined. It can be seen from FIGS. 1A, 1B, and 1C, after addition of Dox, leukemic cells in the spleen and bone marrow of the mice become undetectable. It indicated that high expression of OSKM in the leukemic cells directly led to the elimination of leukemic cells in-vivo.

Figure 2A:
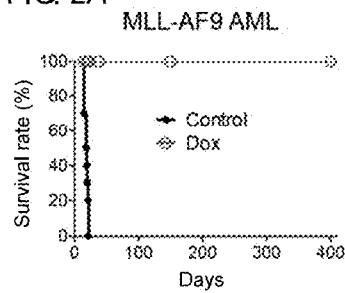
FIGS. 2A, 2B, and 2C—Analysis on survival of leukemic mice after adding Dox into the drinking water for various types of leukemic mice.
Figure 2B:
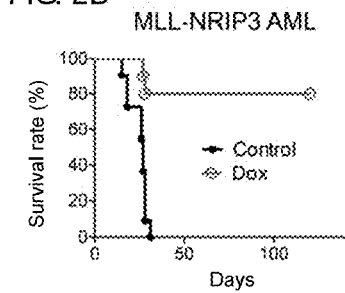
Figure 2C:
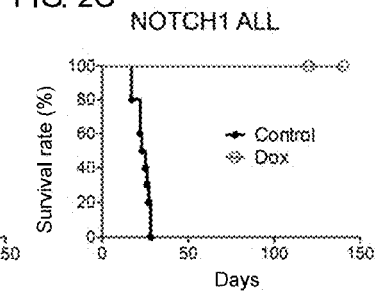

4. Elimination of multiple types of leukemic cells in-vivo: same method was applied to establish another two types of leukemia models: the acute myeloid leukemia (AML) induced by MLL-NRIP3 and acute lymphoblastic leukemia (ALL) induced by NOTCH1. The survival curves are as shown in FIGS. 2A, 2B, and 2C, in which FIG. 2A showed the AML model induced by MLL-AF9, the results of the survival curves demonstrated that all the mice in the control group died of leukemia while all the mice in the experimental group survived. FIG. 2B showed the AML model induced by MLL-NRIP3, the results of the survival curve demonstrated that all the mice in the control group died of leukemia while only a small number of mice in the experimental group died. FIG. 2C showed the ALL model induced by NOTCH1, the results of the survival curve demonstrated that all the mice in the control group died of leukemia but all the mice in the experimental group survived. It can be seen from FIGS. 2A, 2B, and 2C that similar to the leukemia model induced by MLL-AF9, after Dox was added in the drinking water of the mice in the experimental group (for 7 consecutive days), the other two types of leukemic cells can also be eliminated and the leukemia was treated. It indicated utilization of OSKM reprogramming factors was able to eliminate multiple types of leukemias in-vivo.

Figure 3A:
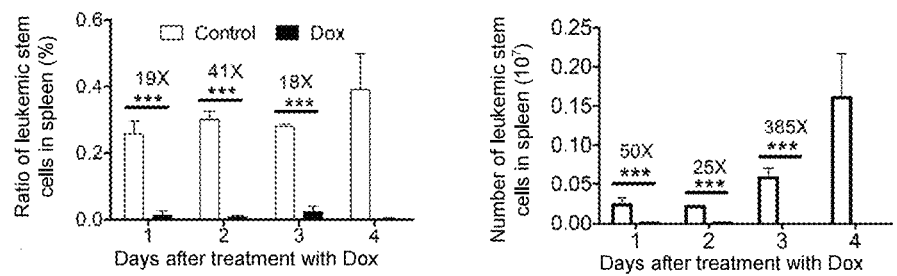
FIGS. 3A and 3B—Analysis on ratio and number of leukemic stem cells in mouse spleen and bone marrow after adding Dox into the drinking water of leukemic mice.
Figure 3B:
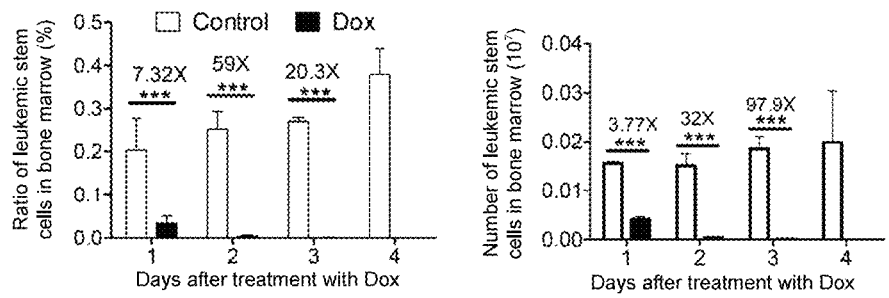

5. Effective elimination of leukemic stem cells: after Dox was added into the drinking water for 1-4 days, flow cytometry was used to determine the ratio of leukemic stem cells. The results are as shown in FIGS. 3A and 3B (FIG. 3A showed the ratio and number of the leukemic stem cells in spleen and FIG. 3B showed the ratio and number of the leukemic stem cells in bone marrow). It can be seen from FIGS. 3A and 3B that compared to mature leukemic cells, elimination of the leukemic stem cells was more rapid.

Figure 4A:
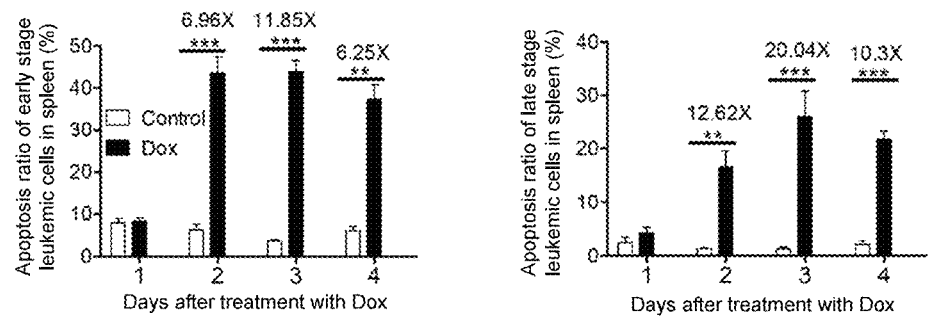
FIGS. 4A and 4B—Analysis on apoptosis of leukemic cells in mouse spleen and bone marrow after adding Dox into the drinking water of leukemic mice.
Figure 4B:
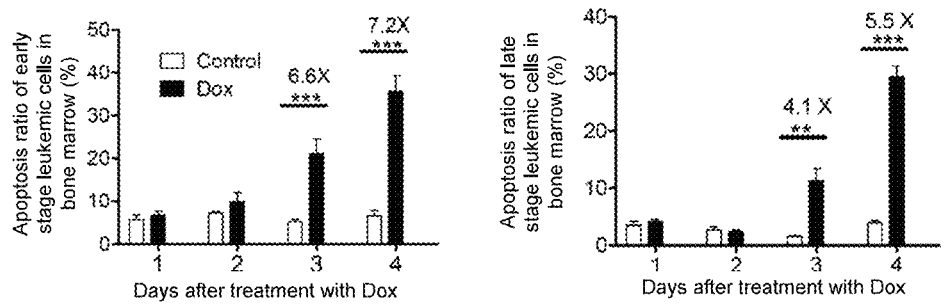

6. Reprogramming factors induced apoptosis of leukemic cells: after Dox was added into the drinking water of experimental group for 1-4 days, flow cytometry was used to analyze the apoptosis of leukemic cells. The results are as shown in FIGS. 4A and 4B, in which FIG. 4A showed the apoptosis ratios of the leukemic cells in spleen in the early stage and the late stage of leukemia after Dox treatment and FIG. 4B showed the apoptosis ratios of the leukemic cells in bone marrow in the early stage and the late stage of leukemia after Dox treatment. It can be seen from FIGS. 4A and 4B that OSKM was able to effectively induce the apoptosis of leukemic cells in-vivo.

Figure 5A:
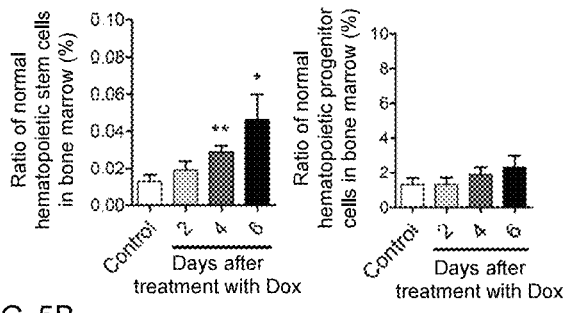
FIGS. 5A, 5B, and 5C—Analysis on ratio and apoptosis of normal hematopoietic stem cells/progenitor cells in mouse bone marrow, and survival analysis of leukemic mice, in which OSKM mice were co-transplanted with normal bone marrow cells and leukemic cells, after the mice developed leukemia, Dox was added into the drinking water for the leukemic mice.
Figure 5B:
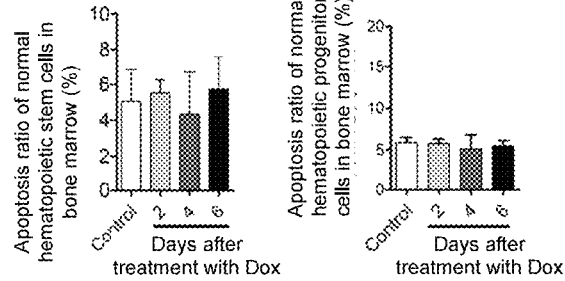
Figure 5C:
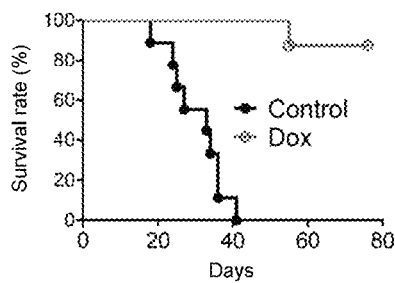
Figure 6A:
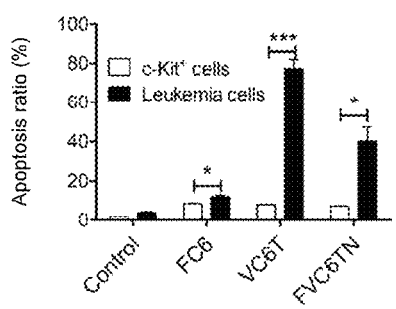
FIGS. 6A, 6B, 6C, 6D, and 6E—Analysis on apoptosis and proliferation of normal hematopoietic stem cells/progenitor cells and leukemic cells after treated with small reprogramming molecules in-vitro and analysis on pathogenic ability of the treated leukemic cells.
Figure 6B:
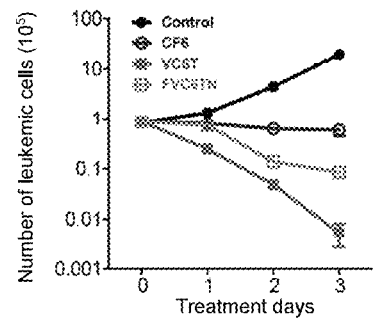
Figure 6C:
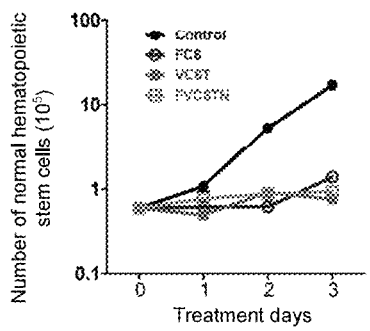
Figure 6D:
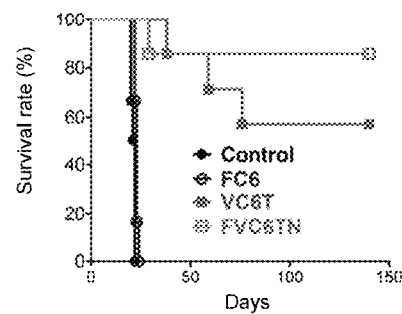
Figure 6E:
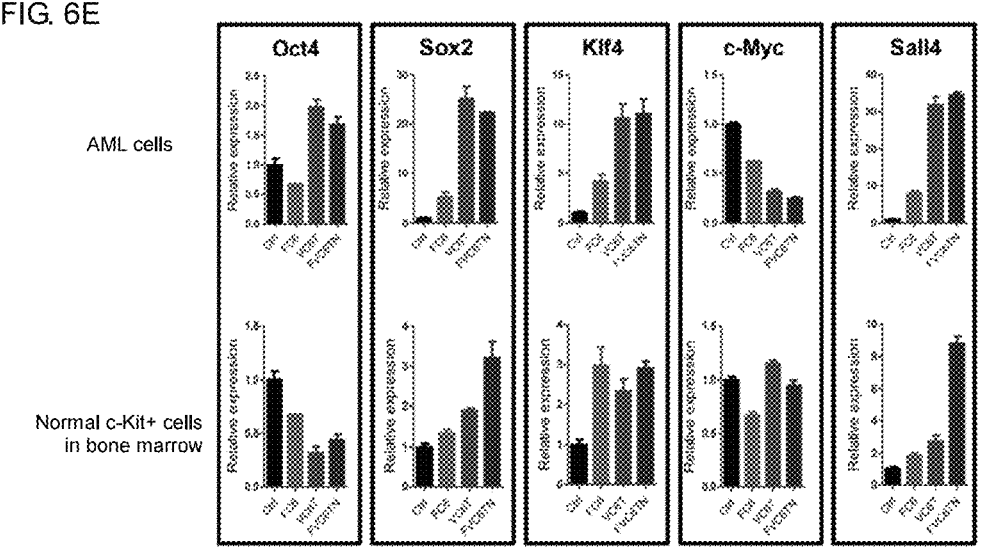

7. Reprogramming factors have less effect on normal hematopoietic stem cells/progenitor cells: bone marrow cells and leukemic cells of OSKM mice were co-transplanted into lethally irradiated mice. After leukemia developed in the mice, Dox was added into the drinking water of the mice in experimental group for 7 days. The results are as shown in FIGS. 5A, 5B, and 5C. FIG. 5A showed the ratios of normal hematopoietic stem cells and progenitor cells in the bone marrow. It can be seen from FIG. 5A that the ratios of normal hematopoietic stem cells and progenitor cells in the mouse bone marrows were not affected after Dox treatment. FIG. 5B showed the apoptosis ratios of normal hematopoietic stem cells and progenitor cells in the bone marrows. It can be seen from FIG. 5B that the apoptosis of normal hematopoietic stem cells and progenitor cells was not affected after Dox treatment. FIG. 5C showed the survival curve of mice, in which except one, all the leukemic mice in experimental group were cured. It can be seen from FIGS. 5A, 5B, and 5C that the number and apoptosis of normal hematopoietic stem cells/progenitor cells were not affected and the mice in the experimental group were recovered from leukemia.

8. Utilization of small reprogramming molecules to induce the elimination of mouse leukemic cells: the small reprogramming molecules include forskolin (FSK, F), VPA (V), CHIR99021 (CHIR, C), RepSox (616452, 6), tranylcypromine (TCP, T) and TTNPB (N). Different combinations were used to treat the leukemic cells and the normal hematopoietic stem cells/progenitor cells in-vitro.

Treatment conditions: initial number of the mouse leukemic cells is $1\times10^5$. Culture medium: IMDM+15% fetal bovine serum+10 ng/ml mouse IL-6+10 ng/ml mouse IL-3+50 ng/ml mouse SCF.

Initial number of the c-Kit+hematopoietic stem cells/progenitor cells is $8\times10^4$. Culture medium: IMDM+15% fetal bovine serum+10 ng/ml mouse IL-6+10 ng/mL mouse IL-3+50 ng/ml mouse SCF+20 ng/ml mouse TPO+10 ng/ml mouse Flt3-L.

Concentration of small reprogramming molecules: forskolin (10 μM), VPA (500 μM), CHIR99021 (10 μM), RepSox (5 μM), tranylcypromine (5 μM) and TTNPB (1 μM).

The results are as shown in FIGS. 6A, 6B, 6C, 6D, and 6E. It can be seen from FIG. 6A that after treating with various combinations of small reprogramming molecules, apoptosis of the leukemic cells was significantly increased, while giving less effect on the normal hematopoietic stem cells/progenitor cells. It can be seen from FIG. 6B that after treating the leukemic cells with the small reprogramming molecules, cell proliferation was significantly suppressed, and the number of cells was significantly decreased compared to pre-treatment (day 0). It can be seen from FIG. 6C that proliferation of normal hematopoietic stem cells/progenitor cells was also suppressed after treated with the small reprogramming molecules, but the number of the cells was slightly increased compared to pre-treatment (day 0). It can be seen from FIG. 6D that pathogenicity of same number of the leukemic cells is significantly reduced after treated with two combinations of VC6T and FVC6TN, and leukemia was not developed in most of the mice. It can be seen from FIG. 6E that expression of pluripotency genes in the cells was increased after treating the cells with the small reprogramming molecules, indicating the initiation of reprogramming process. It can be seen from FIGS. 6A, 6B, 6C, 6D, and 6E that small reprogramming molecules was able to cause selective elimination of mouse leukemic cells in-vivo/in-vitro, and caused less intervention on normal hematopoietic stem cells/progenitor cells and can effectively treat the mouse leukemia.

Embodiment 2

Utilization of Small Reprogramming Molecules to Induce the Elimination of Human Leukemic Cells In-Vitro 1. Human leukemic cell lines: a variety of leukemic cell lines were treated with the small reprogramming molecules and their apoptosis levels and growth condition were determined.

Treatment conditions: the initial cell number was $1\times10^5$.

HL-60, K562, NB4, Kasumi-1 and Jurkat cells: RPMI 1640+10% fetal bovine serum

THP-1 cells: RPMI 1640+10% fetal bovine serum+0.05 mM 2-mercaptoethanol

KG-1 and KG-1a cells: IMDM+20% fetal bovine serum

Concentration of small reprogramming molecules: forskolin (10 µM), VPA (500 µM), CHIR99021 (10 µM), RepSox (5 µM), tranylcypromine (5 µM) and TTNPB (1 µM)

Figure 7A:
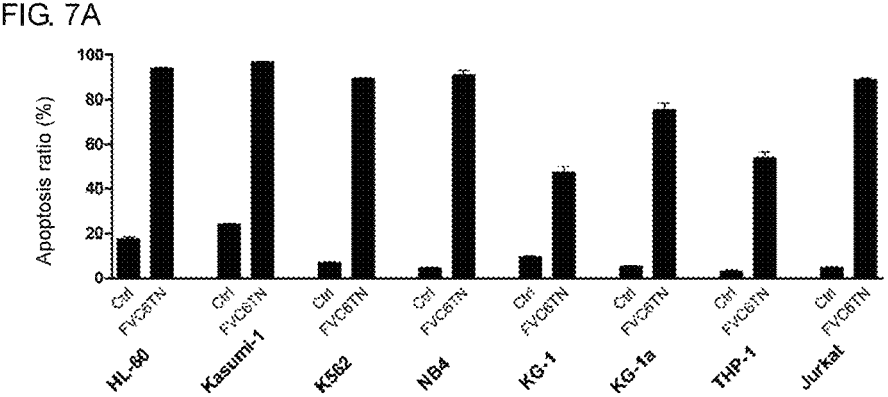
FIGS. 7A and 7B—Analysis on apoptosis and proliferation of human leukemic cell lines after treated with small reprogramming molecules.
Figure 7B:
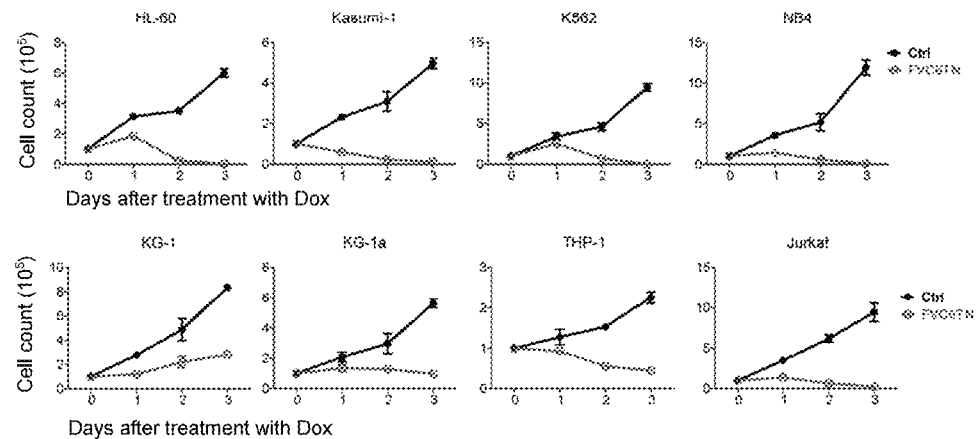

The results are as shown in FIGS. 7A and 7B, in which after treated with combination of small reprogramming molecules FVC6TN, apoptosis was increased in all the leukemic cell lines and cell growth was severely suppressed.

2. Specimen of leukemia patients: total of 22 cases of acute myelogenous leukemia (AML) patient cells and 5 cases of normal human umbilical cord blood stem cells (CD34+) were collected for the present experiment. Small reprogramming molecules were used for drug treatment under the culture condition in-vitro.

Treatment conditions: initial number of CD34+ cells of human umbilical cord blood and CD34+ cells of AML patients were $1\times10^5$. Culture medium: IMDM+15% fetal bovine serum+1% double antibiotic+100 ng/ml human SCF+100 ng/ml human Flt3-L+50 ng/ml human TPO+10 ng/ml human IL-3+100 ng/ml human IL-6

Concentration of small reprogramming molecules: forskolin (10 µM), VPA (500 µM), CHIR99021 (10 µM), RepSox (5 µM), tranylcypromine (5 µM) and TTNPB (1 µM)

Figure 8A:
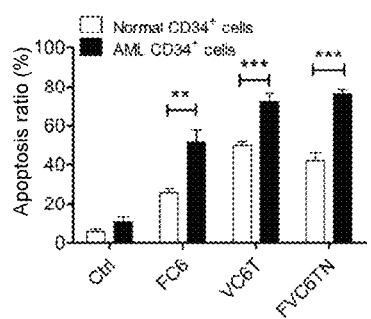
FIGS. 8A, 8B, 8C, and 8D—Analysis on apoptosis and colony formation ability of CD34+ cells from human umbilical cord blood and CD34+ cells from AML patient after treated with small reprogramming molecules.
Figure 8B:
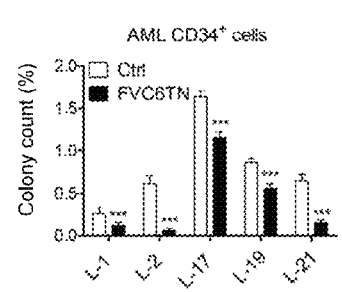
Figure 8C:
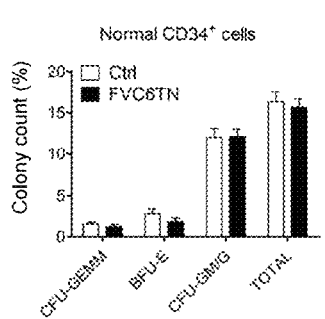
Figure 8D:
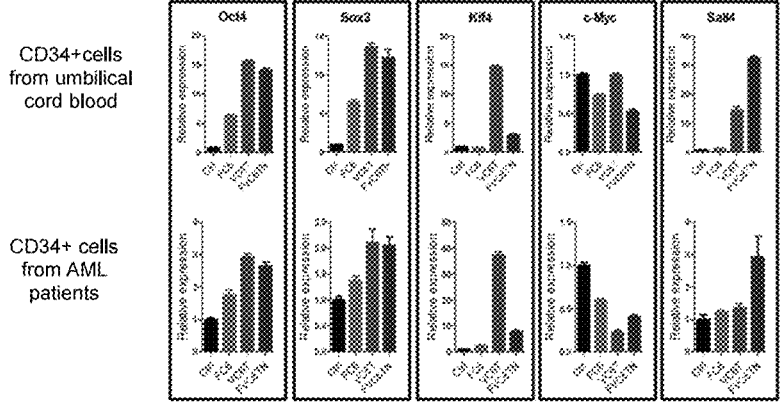

The results are as shown in FIGS. 8A, 8B, 8C, and 8D. FIG. 8A showed the apoptosis ratios of CD34+ cells from human umbilical cord blood and CD34+ cells from AML patients after treated with various combinations of small reprogramming molecules. It can be seen from FIG. 8A that after treated with the combination of small reprogramming molecules, apoptosis of CD34+ cells of AML patients was more significant compared to CD34+ cells of human umbilical cord blood. FIGS. 8B and 8C respectively showed the colony number of CD34+ cells of AML patients and CD34+ cells of human umbilical cord blood, respectively after treated with combination of small reprogramming molecules FVC6TN. It can be seen from FIG. 8B that after treated with the combination of small reprogramming molecules FVC6TN, colony formation ability of CD34+ cells of AML patients was significantly reduced (L1, L2, L17, L19 and L21 were the patient number). It can be seen from FIG. 8C that after treated with the combination of small reprogramming molecules FVC6TN, colony formation ability of CD34+ cells of human umbilical cord blood was not significantly affected after the treatment with the combination of small molecules. It can be seen from FIG. 8D that after the cells were treated with the combination of small reprogramming molecules, expression of intracellular pluripotency genes was increased indicating the initiation of reprogramming process. It can be seen from FIGS. 8A, 8B, 8C, and 8D that compared to CD34+ cells of normal umbilical cord blood, apoptosis level of CD34+ cells of AML patients was significantly increased. The in-vitro colony-forming cell (CFC) assay indicated that after treated with the small reprogramming molecules, the colony forming ability of CD34+ cells of AML patients was severely suppressed, and the colony forming ability of CD34+ cells of normal umbilical cord blood was not affected.

Similar to the mouse models, reprogramming factors were able to selectively induce the cell death of human leukemic cells in-vitro, and the effect on normal hematopoietic stem cells/progenitor cells was relatively low, so as the effect of cleansing of leukemic cells can be achieved.

What is claimed is:

1. A method for eliminating leukemic cells in-vivo, comprising the following steps:
    a) preparing a leukemia retrovirus comprising an MLL-AF9 gene;
    b) collecting bone marrow cells from an all-iPS mouse expressing somatic cell reprogramming inducing factors Oct-4, Sox-2, Klf4 and c-Myc;
    c) enriching and isolating lineage-negative (Lin−) bone marrow cells from said bone marrow cells from b) using magnetic beads, wherein the enriched and isolated bone marrow cells express somatic cell reprogramming inducing factors Oct-4, Sox-2, Klf4 and c-Myc, and the expression of said somatic cell reprogramming inducing factors is induced by doxycycline;
    d) infecting the lineage-negative (Lin−) bone marrow cells from c) with the leukemia retrovirus from a);
    e) transplanting the infected lineage-negative (Lin−) bone marrow cells from d) into a C57BL/6J mouse that has been exposed to radiation, whereby said mouse produces leukemic cells;
    f) collecting leukemic cells from the mouse of e);
    g) adding doxycycline into the drinking water of the mouse of e) to induce expression of the somatic cell reprogramming inducing factors in the leukemic cells, wherein the expression of the somatic cell reprogramming inducing factors eliminates leukemic cells;
    h) collecting blood from the spleen and bone marrow of the mouse from step g) and monitoring the ratio of leukemic cells to non-leukemic cells in the collected blood.

2. The method according to claim 1, wherein the somatic cell reprogramming inducing factors are in a form of cDNA or mRNA.

3. The method according to claim 1, wherein the somatic cell reprogramming inducing factors Oct-4, Sox-2, Klf4 and c-Myc promote leukemic cells to initiate process of somatic cell reprogramming.

4. The method according to claim 3, wherein the somatic cell reprogramming inducing factors are in a form of cDNA or mRNA.

5. A method of eliminating multiple types of leukemic cells in-vivo, comprising the following steps:
  a) preparing multiple types of leukemia retroviruses, wherein each of the multiple types of leukemia retroviruses comprises an MLL-AF9 gene, an MLL-NRIP3 gene, and a NOTCH-1 gene, respectively;
  b) collecting bone marrow cells from an all-iPS mouse expressing somatic cell reprogramming inducing factors Oct-4, Sox-2, Klf4 and c-Myc;
  c) enriching and isolating lineage-negative (Lin−) bone marrow cells from said bone marrow cells from b) using magnetic beads, wherein the enriched and isolated bone marrow cells express somatic cell reprogramming inducing factors Oct-4, Sox-2, Klf4 and c-Myc, and the expression of said somatic cell reprogramming inducing factors is induced by doxycycline;
  d) dividing the enriched, isolated Lin-bone marrow cells from c) into groups and infecting each of the groups with the multiple types of leukemia retroviruses from a);
  e) transplanting the infected lineage-negative (Lin−) bone marrow cells from d) into a C57BL/6J mouse that has been exposed to radiation, whereby said mouse produces leukemic cells;
  f) collecting leukemic cells expressing the MLL-AF9 gene, MLL-NRIP3 gene, and NOTCH-1 gene from the mouse of e);
  g) adding doxycycline into the drinking water of the mouse of e) to induce expression of the somatic cell reprogramming inducing factors in the leukemic cells, wherein the expression of the somatic cell reprogramming inducing factors eliminates leukemic cells;
  h) collecting blood from the spleen and bone marrow of the mouse of g) and monitoring the ratio of leukemic cells to non-leukemic cells expressing the MLL-AF9 gene, the ratio of leukemic cells to non-leukemic cells expressing the MLL-NRIP3 gene, and the ratio of leukemic cells to non-leukemic cells expressing the NOTCH-1 gene in the collected blood.

6. A method for eliminating leukemic stem cells in-vivo, comprising the following steps:
  a) preparing a leukemia retrovirus comprising an MLL-AF9 gene;
  b) collecting bone marrow cells from an all-iPS mouse expressing somatic cell reprogramming inducing factors Oct-4, Sox-2, Klf4 and c-Myc;
  c) enriching and isolating lineage-negative (Lin−) bone marrow cells from said bone marrow cells from b) using magnetic beads; wherein the enriched and isolated bone marrow cells express somatic cell reprogramming inducing factors Oct-4, Sox-2, Klf4 and c-Myc, and the expression of said somatic cell reprogramming inducing factors is induced by doxycycline;
  d) infecting the lineage-negative (Lin−) bone marrow cells from c) with the leukemia retrovirus from a);
  e) transplanting the infected lineage-negative (Lin−) bone marrow cells from d) into a C57BL/6J mouse that has been exposed to radiation, whereby said mouse produces leukemic stem cells;
  f) collecting leukemic stem cells from the mouse of e);
  g) adding the doxycycline into the drinking water of the mouse of e) to induce expression of the somatic cell reprogramming inducing factors in the leukemic stem cells, wherein the expression of the somatic cell reprogramming inducing factors eliminates leukemic stem cells;
  h) collecting blood from the spleen and bone marrow of the mouse of g) and monitoring the ratio of leukemic stem cells to non-leukemic stem cells in the collected blood.

* * * * *

UNITED STATES PATENT AND TRADEMARK OFFICE
CERTIFICATE OF CORRECTION

PATENT NO. : 10,799,474 B2
APPLICATION NO. : 15/751166
DATED : October 13, 2020
INVENTOR(S) : Tao Cheng et al.

Page 1 of 1

It is certified that error appears in the above-identified patent and that said Letters Patent is hereby corrected as shown below:

On the Title Page

Item [73] should read: Institute of Hematology and Blood Diseases Hospital, CAMS & PUMC, Tianjin (CN)

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*